(12) United States Patent
Moodie

(10) Patent No.: US 8,527,217 B2
(45) Date of Patent: Sep. 3, 2013

(54) APPARATUS AND METHOD FOR PHYSICAL EVALUATION

(75) Inventor: Patrick Moodie, Lawrence, KS (US)

(73) Assignee: Dynamic Athletic Research Institute, LLC, Kansas City, KS (US)

( * ) Notice: Subject to any disclaimer, the term of this patent is extended or adjusted under 35 U.S.C. 154(b) by 344 days.

(21) Appl. No.: 12/876,972

(22) Filed: Sep. 7, 2010

(65) Prior Publication Data

US 2011/0060537 A1 Mar. 10, 2011

Related U.S. Application Data

(60) Provisional application No. 61/240,482, filed on Sep. 8, 2009.

(51) Int. Cl.
*B25B 23/14* (2006.01)
*G01L 3/00* (2006.01)

(52) U.S. Cl.
USPC .............. 702/41; 706/12; 706/45; 600/595; 600/407; 600/449

(58) Field of Classification Search
USPC .......................................................... 702/41
See application file for complete search history.

(56) References Cited

U.S. PATENT DOCUMENTS

| | | | | |
|---|---|---|---|---|
| 1,985,478 A * | 12/1934 | Yuasa | | 73/12.13 |
| 4,954,964 A * | 9/1990 | Singh | | 706/11 |
| 6,050,962 A * | 4/2000 | Kramer et al. | | 600/595 |
| 6,428,490 B1 * | 8/2002 | Kramer et al. | | 600/595 |
| 6,765,726 B2 * | 7/2004 | French et al. | | 359/630 |
| 7,070,571 B2 * | 7/2006 | Kramer et al. | | 600/595 |
| 7,203,274 B2 * | 4/2007 | Charles et al. | | 378/54 |
| 7,441,953 B2 * | 10/2008 | Banks | | 378/197 |
| 7,826,641 B2 * | 11/2010 | Mandella et al. | | 382/106 |
| 7,880,770 B2 * | 2/2011 | Alvarez et al. | | 348/211.7 |
| 8,055,021 B2 * | 11/2011 | Caritu et al. | | 382/103 |
| 8,078,321 B2 * | 12/2011 | Iba | | 700/253 |
| 8,099,374 B2 * | 1/2012 | Iba | | 706/12 |
| 8,165,844 B2 * | 4/2012 | Luinge et al. | | 702/152 |
| 2005/0015002 A1 * | 1/2005 | Dixon et al. | | 600/407 |
| 2005/0113691 A1 * | 5/2005 | Liebschner | | 600/437 |
| 2006/0001545 A1 * | 1/2006 | Wolf | | 340/573.1 |
| 2006/0015372 A1 * | 1/2006 | Graham | | 705/3 |
| 2007/0003915 A1 * | 1/2007 | Templeman | | 434/247 |
| 2008/0033283 A1 * | 2/2008 | Dellaca et al. | | 600/424 |
| 2008/0037701 A1 * | 2/2008 | Banks | | 378/11 |
| 2008/0221487 A1 * | 9/2008 | Zohar et al. | | 600/595 |
| 2008/0252445 A1 * | 10/2008 | Kolen | | 340/539.16 |
| 2008/0278497 A1 * | 11/2008 | Jammes et al. | | 345/474 |
| 2008/0285805 A1 * | 11/2008 | Luinge et al. | | 382/107 |
| 2008/0312770 A1 * | 12/2008 | Alvarez et al. | | 700/251 |
| 2008/0312772 A1 * | 12/2008 | Hasegawa et al. | | 700/260 |

(Continued)

*Primary Examiner* — Tung S Lau
*Assistant Examiner* — Stephanie Chang
(74) *Attorney, Agent, or Firm* — Husch Blackwell LLP

(57) ABSTRACT

A physical evaluation apparatus includes a kinematic data capture device, the kinematic data capture device being configured and disposed to obtain whole body kinematic data from a subject. The kinematic data capture device is further configured to obtain dimensions of at least one body segment. A mass data capture device is configured and disposed to obtain mass data on the subject, the mass data being separable according to body segments of a subject to yield segment mass data. A processor, is configured to calculate the force being generated by a subject of the evaluation apparatus at selectable positions or in a selectable direction. The force is calculated without a force plate.

18 Claims, 7 Drawing Sheets

(56) References Cited

U.S. PATENT DOCUMENTS

| | | | |
|---|---|---|---|
| 2009/0066700 A1* | 3/2009 | Harding et al. | 345/473 |
| 2009/0234251 A1* | 9/2009 | Bhattacharya et al. | 600/595 |
| 2009/0310826 A1* | 12/2009 | Kroger | 382/110 |
| 2011/0025685 A1* | 2/2011 | Epps | 345/419 |
| 2011/0060537 A1* | 3/2011 | Moodie | 702/41 |
| 2012/0078416 A1* | 3/2012 | Iba et al. | 700/246 |
| 2012/0159290 A1* | 6/2012 | Pulsipher et al. | 714/819 |

\* cited by examiner

| PATIENT: | MOODIE, PATRICK G. | | FACILITY ID: | | |
|---|---|---|---|---|---|
| BIRTH DATE: | 3/16/1983  22.8 YEARS | | PHYSICIAN: | | |
| HEIGHT/WEIGHT: | 70.5 IN.  196.8 LBS. | | MEASURED: | 2/3/2006  10:34:32 AM {8.80} | |
| SEX/ETHNIC: | MALE  WHITE | | ANALYZED: | 2/3/2006  10:34:33 AM {8.80} | |

BODY COMPOSITION

| REGION | TISSUE | REGION | TISSUE | FAT | LEAN | BMC | TOTAL MASS |
|---|---|---|---|---|---|---|---|
| LEFT ARM | 19.3 | 18.6 | 6,359 | 1,235 | 5,124 | 277 | — |
| LEFT LEG | 22.2 | 21.3 | 14,154 | 3,148 | 11,006 | 852 | — |
| LEFT TRUNK | 29.2 | 28.2 | 19,710 | 5,750 | 13,960 | 658 | — |
| LEFT TOTAL | 24.5 | 23.5 | 42,286 | 10,378 | 31,908 | 1,826 | — |
| RIGHT ARM | 19.4 | 18.4 | 5,786 | 1,120 | 4,666 | 314 | — |
| RIGHT LEG | 22.3 | 21.3 | 14,468 | 3,223 | 11,245 | 691 | — |
| RIGHT TRUNK | 29.2 | 28.3 | 19,760 | 5,760 | 14,000 | 683 | — |
| RIGHT TOTAL | 24.4 | 33.3 | 42,816 | 10,439 | 32,407 | 2,004 | — |
| ARMS | 19.4 | 18.5 | 12,144 | 2,355 | 9,789 | 591 | — |
| LEGS | 22.3 | 21.3 | 28,623 | 6,372 | 22,251 | 1,343 | — |
| TRUNK | 29.2 | 28.2 | 39,470 | 11,510 | 27,960 | 1,340 | — |
| ANDROID | 33.3 | 32.8 | 5,850 | 1,940 | 3,904 | 77 | — |
| GYNOID | 28.3 | 27.4 | 14,249 | 4,021 | 10,228 | 432 | — |
| TOTAL | 24.5 | 23.4 | 85,132 | 20,817 | 64,315 | 3,830 | 59.0 |

MASS RATIOS

| TRUNK/TOTAL | LEGS/TOTAL | (ARMS+LEGS)/TRUNK |
|---|---|---|
| 0.55 | 0.31 | 0.76 |

FIG. 4

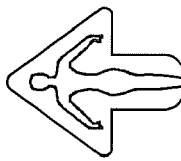

ATHLETE NAME:

MOTION: RANGE OF MOTION

| | | | | |
|---|---|---|---|---|
| WRISTS | | | | |
| LEFT WRIST | 53.38 DEG UP | 17.14 DEG DOWN | | |
| RIGHT WRIST | 35.51 DEG UP | 8.19 DEG DOWN | | |
| ELBOWS | | | | |
| LEFT ELBOW | 188.27 | 81.27 | 107.10 DEG | |
| RIGHT ELBOW | 178.42 | 82.90 | 115.52 DEG | |
| SHOULDER ABDUCTION | | | | |
| LEFT SHOULDER | 179.98 | 23.15 | 66.04 | 90.69 DEG |
| RIGHT SHOULDER | 153.59 | 44.34 | 52.15 | 57.09 DEG |
| SHOULDER HORIZONTAL ROTATION | | | | |
| LEFT SHOULDER | 121.12 | 167.00 | 55.39 | 9.50 DEG |
| RIGHT SHOULDER | 194.08 | 103.22 | 60.32 | 30.51 DEG |
| TRUNK ROTATION | | | | |
| RIGHT ROTATION | 41.83 DEG | | | |
| LEFT ROTATION | 38.15 DEG | | | |
| LEFT SHOULDER TO RIGHT KNEE | | | | |
| LEFT SHOULDER | 100.72 | 175.47 | 74.75 DEG | |
| TRUNK | 59.72 | 75.93 | 18.21 DEG | |
| HIPS | 0.06 | 0.00 | 75.38 DEG | |
| RIGHT SHOULDET TO LEFT KNEE | | | | |
| RIGHT SHOULDER | 79.53 | 145.22 | 65.59 DEG | |
| TRUNK | 57.53 | 75.37 | 65.69 DEG | |
| HIPS | -0.06 | 0.01 | 120.65 DEG | |

| | | |
|---|---|---|
| SQUAT | | |
| RIGHT HIP | 89.71 | 178.91 109.20 DEG |
| LRFT HIP | 110.88 | 197.01 86.15 DEG |
| RIGHT KNEE | 78.43 | 181.23 102.80 DEG |
| LEFT KNEE | 112.88 | 204.49 91.61 DEG |
| LEFT ANKLE | 82.68 | 111.04 28.46 DEG |
| RIGHT ANKLE | 75.91 | 98.18 22.26 DEG |
| RIGHT TRUNK | 22.15 | 93.94 71.79 DEG |
| LEFT TRUNK | 13.27 | 86.87 53.41 DEG |
| FORWARD LEAN RIGHT | -0.09 | -0.43 -0.34 M |
| FORWARD LEAN LEFT | -0.08 | -0.48 -0.27 M |
| STRAIGHT LUNGE LEFT | | STRAIGHT LUNGE RIGHT |
| LEFT HIP 120.11 DEG | | RIGHT HIP 101.44 DEG |
| LEFT KNEE 108.34 DEG | | RIGHT KNEE 93.31 DEG |
| LEFT ANKLE 95.71 DEG | | RIGHT ANKLE 91.21 DEG |
| TRUNK 63.77 DEG | | TRUNK 59.71 DEG |
| STRIDE 1.17 -0.43 M | | STRIDE -1.09 -0.02 M |
| VERTICAL JUMP | | |
| LEFT HIP 132.93 DEG | | RIGHT HIP 85.99 DEG |
| LEFT KNEE 122.63 DEG | | RIGHT KNEE 110.48 DEG |
| LEFT ANKLE 69.87 DEG | | RIGHT ANKLE 81.51 DEG |
| TRUNK 19.27 DEG | | VERT LEAP 0.72 M |

FIG. 5

ATHLETE NAME:
MOTION: QUARTER BACK THROW - RIGHT HANDED
MOTION GROUP: 2

| TIME PHASE ENDS | COCKING | | | ACCELERATION | | | 0.25 SEC | DECELERATION | | | 0.07 SEC |
|---|---|---|---|---|---|---|---|---|---|---|---|
| | AVG | MIN | MAX | | AVG | MIN | MAX | | AVG | MIN | MAX |
| RIGHT ARM | | | | | | | | | | | |
| WRIST ANGLE | 103.08 | 47.59 | 129.10 DEG | | 116.48 | 35.08 | 134.22 DEG | | 110.02 | 34.93 | 137.37 DEG |
| ELBOW ANGLE | 98.31 | 85.37 | 112.05 DEG | | 144.35 | 133.39 | 157.20 DEG | | 164.00 | 157.38 | 173.71 DEG |
| SHOULDER ABDUCTION | 97.99 | 72.82 | 121.79 DEG | | 109.96 | 105.71 | 113.24 DEG | | 121.32 | 97.23 | 136.68 DEG |
| HORIZONTAL ROTATION | 132.56 | 127.87 | 151.08 DEG | | 153.21 | 151.52 | 155.99 DEG | | 171.18 | 164.71 | 177.61 DEG |
| RIGHT ARM FORCES | | | | | | | | | | | |
| WRIST JOINT TORQUE | 0.71 | -0.38 | 2.07 Nm | | 0.09 | -6.54 | 7.40 Nm | | 4.14 | -0.06 | 11.62 Nm |
| ELBOW JOINT TORQUE | 5.70 | 1.05 | 8.47 Nm | | -11.78 | -32.06 | 10.83 Nm | | 9.23 | -85.72 | 41.96 Nm |
| SHOULDER JOIT TORQUE | 4.65 | 0.45 | 8.01 Nm | | -13.13 | -30.01 | 6.07 Nm | | -18.69 | -67.69 | 8.69 Nm |
| KNEES | | | | | | | | | | | |
| LEFT KNEE ANGLE | 174.27 | 168.82 | 191.02 DEG | | 201.12 | 197.22 | 204.21 DEG | | 194.73 | 189.47 | 199.82 DEG |
| RIGHT KNEE ANGLE | 173.25 | 168.18 | 179.58 DEG | | 156.42 | 149.59 | 163.02 DEG | | 145.00 | 138.66 | 148.74 DEG |
| HIPS | | | | | | | | | | | |
| LEFT HIP ANGLE | 222.99 | 215.98 | 227.39 DEG | | 192.38 | 189.47 | 194.65 DEG | | 194.96 | 193.84 | 196.99 DEG |
| RIGHT HIP ANGLE | 181.91 | 153.77 | 184.81 DEG | | 176.06 | 171.67 | 180.29 DEG | | 171.75 | 167.36 | 174.42 DEG |
| LEFT LEG FORCES | | | | | | | | | | | |
| LEFT ANKLE JOINT TORQUE | 20.06 | -3.10 | 66.82 Nm | | 109.47 | 82.41 | 127.36 Nm | | 127.93 | 110.60 | 144.95 Nm |
| LEFT KNEE JOINT TORQUE | -101.64 | -187.45 | 92.17 Nm | | 151.91 | 102.56 | 210.63 Nm | | 230.34 | 153.88 | 297.07 Nm |
| LEFT HIP JOINT TORQUE | -184.27 | -250.60 | -146.65 Nm | | 4.29 | -68.45 | 58.58 Nm | | 72.13 | -17.28 | 181.91 Nm |
| RIGHT LEG FORCES | | | | | | | | | | | |
| RIGHT ANKLE JOINT TORQUE | -6.93 | -20.24 | 17.74 Nm | | -30.12 | -47.77 | -11.70 Nm | | -19.62 | -36.23 | 15.70 Nm |
| RIGHT KNEE JOINT TORQUE | 3.71 | -120.22 | 124.19 Nm | | -172.09 | -227.98 | -127.07 Nm | | -142.97 | -216.28 | -86.03 Nm |
| RIGHT HIP JOINT TORQUE | -57.66 | -150.84 | 92.08 Nm | | -180.20 | -246.92 | -131.51 Nm | | -131.03 | -210.04 | -44.94 Nm |
| BODY WEIGHT DISTRIBUTION | | | | | | | | | | | |
| LEFT FOOT | 66.37% | 63.86% | 71.48% | | 69.83% | 87.32% | 72.60% | | 73.27% | 70.21% | 77.23% |
| | 533.23 | 374.51 | 702.37 | | 1639.39 | 1287.88 | 1446.62 | | 1281.13 | 1118.42 | 1444.01 |
| | 648.75 | 624.11 | 699.70 | | 977.53 | 977.53 | 977.53 | | 977.53 | 977.53 | 977.53 |
| | 33.63% | 28.42% | 36.15% | | 30.17% | 27.50% | 32.68% | | 28.73% | 22.77% | 29.79% |
| | 214.59 | 91.02 | 309.32 | | 395.29 | 325.41 | 470.35 | | 300.31 | 140.70 | 467.06 |
| RIGHT FOOT | 328.78 | 277.83 | 353.42 | | 0.00 | 0.00 | 0.00 | | 0.00 | 0.00 | 0.00 |

FIG. 6

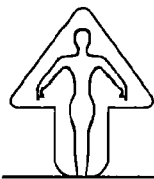

ATHLETE NAME:
MOTION:      GROUP4-WRRUN1

| RANGE OF MOTION | STANCE | PUSH OFF |
|---|---|---|
| LEFT ANKLE | 101.08 DEG | 75.60 DEG |
| RIGHT ANKLE | 89.89 DEG | 110.13 DEG |
| LEFT KNEE | 158.00 DEG | 124.00 DEG |
| RIGHT KNEE | 181.16 DEG | 180.75 DEG |
| LEFT HIP | 178.88 DEG | 177.22 DEG |
| RIGHT HIP | 163.40 DEG | 178.93 DEG |
| TRUNK | 18.76 DEG | 21.07 DEG |
| LEFT SHOULDER | 47.50 DEG | 71.12 DEG |
| RIGHT SHOULDER | 60.19 DEG | 65.51 DEG |
| LEFT ELBOW | 125.09 DEG | 136.31 DEG |
| RIGHT ELBOW | 138.29 DEG | 73.54 DEG |
| LEG FORCES | | |
| LEFT HIP | -42.96 Nm | -488.03 Nm |
| RIGHT HIP | -4.15 Nm | -595.21 Nm |
| LEFT KNEE | 4.12 Nm | -268.64 Nm |
| RIGHT KNEE | -10.39 Nm | -397.21 Nm |
| LEFT ANKLE | 45.16 Nm | 55.08 Nm |
| RIGHT ANKLE | 8.59 Nm | -49.09 Nm |
| BODY WEIGHT DISTRIBUTION | | |
| RIGHT FOOT | 28.24% | 19.14% |
| LEFT FOOT | 71.76% | 80.86% |

FIG. 7

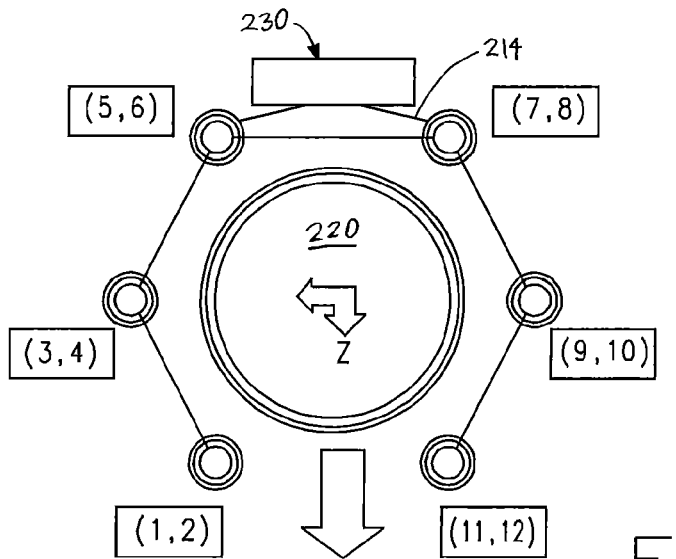

FIG. 8

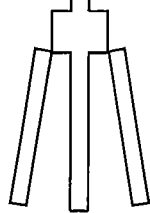
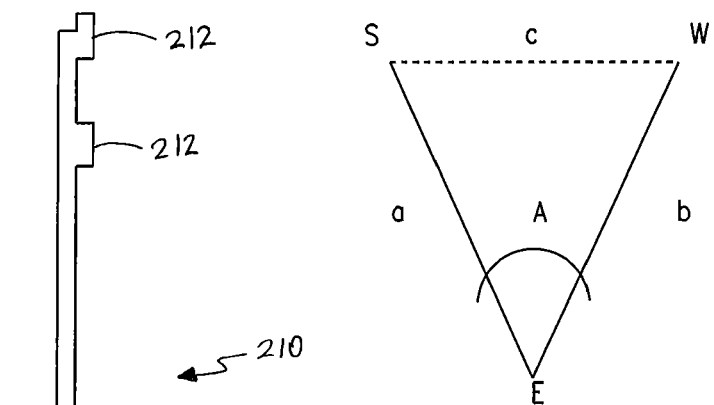
FIG. 9
FIG. 10
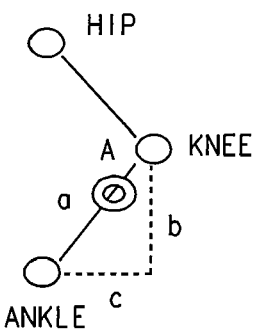
FIG. 11
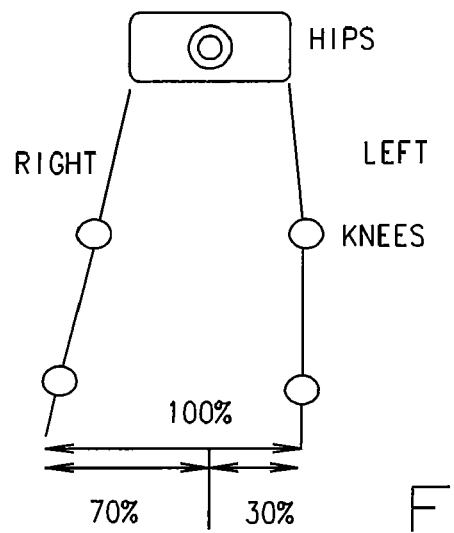
FIG. 12

APPARATUS AND METHOD FOR PHYSICAL EVALUATION

CROSS-REFERENCE TO RELATED APPLICATIONS

This application claims priority to U.S. Provisional Patent application No. 61/240,482 filed Sep. 8, 2009.

BACKGROUND OF THE INVENTION

1. Field of the Invention

The present invention is in the field of therapeutic evaluation of physical subjects in particular humans in athletics.

2. Background

In the world of sports science and medicine different areas of expertise are utilized to ensure that an athlete has the best opportunity to achieve their full potential. Some of these areas of expertise are athletic training, physical therapy, exercise physiology, and team physicians. Currently, each of these professionals assesses the athlete and provides the trainer or coach feedback. Many of the tests performed by these professionals are subjective—relying on the naked eye to examine complex movements. These tests can also be very time consuming and involve tedious measurement methods. Both aspects of current evaluations introduce human error. What can be seen or felt is often debatable and leads to unreliable and unrepeatable methods of testing. Minimal mistakes during these tests or differences between tests can change an athletes report from a label of 'unhealthy' to 'healthy' or vice versa.

Biomechanical analyses is needed to transform normal observations into numbers, and thus turn the subjective into the objective. The athletic trainer, physical therapist, exercise physiologist, and biomechanist all need provide a complete picture of any athlete.

SUMMARY OF THE INVENTION

A physical evaluation apparatus includes a kinematic data capture device, the kinematic data capture device being configured and disposed to obtain whole body kinematic data from a subject. The kinematic data capture device is further configured to obtain dimensions of at least one body segment. A mass data capture device is configured and disposed to obtain mass data on the subject, the mass data being separable according to body segments of a subject to yield segment mass data. A processor, is configured to calculate the force being generated by a subject of the evaluation apparatus at selectable positions or in a selectable direction. The force being calculated without a force plate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 4 is an example data table.
FIG. 5 is an example data table.
FIG. 6 is an example data table.
FIG. 7 is an example data table.
FIG. 8 is a schematic kinematic data capture device and capture zone configuration.
FIG. 9 is a side view of a tripod with cameras.
FIG. 10 is a schematic joint angle.
FIG. 11 is a schematic joint moment.
FIG. 12 is a schematic weight/force distribution

DETAILED DESCRIPTION

Figures 1, 2:
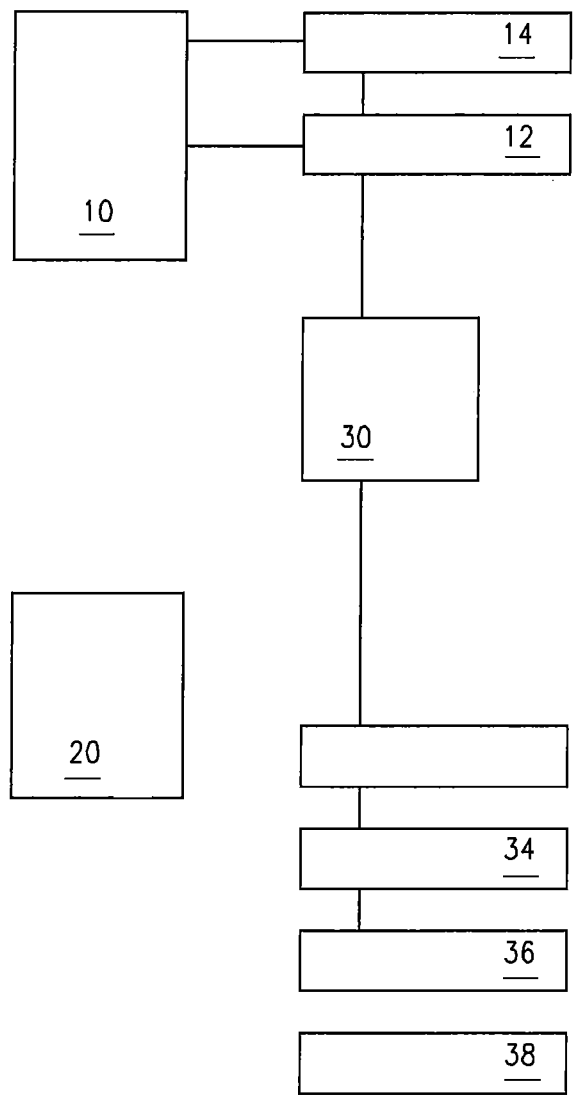
FIG. 1 is block diagram of invention.
FIG. 2 is flow chart of the method of the present invention.
Figure 3:
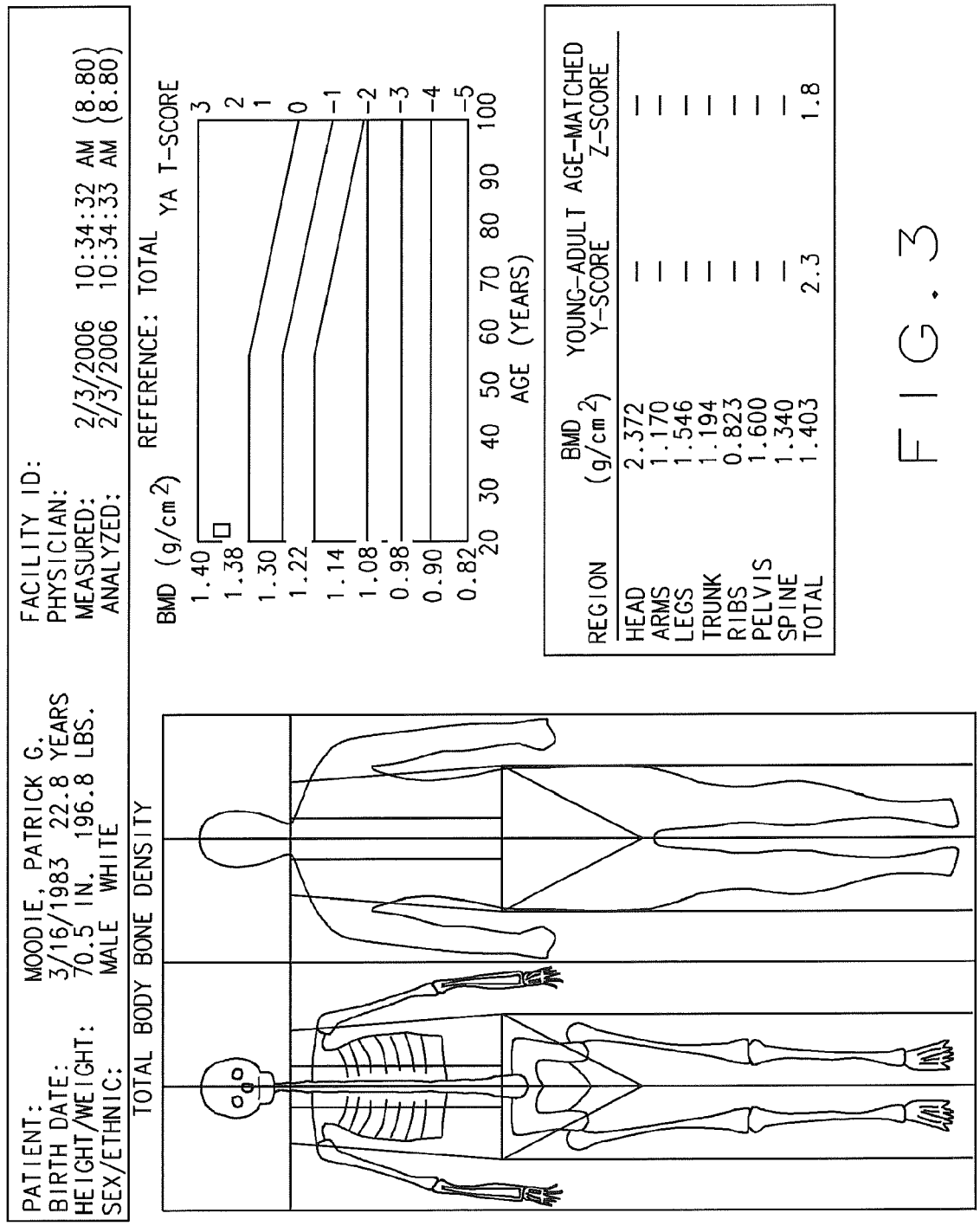
FIG. 3 is an example data table.

Referring now to the drawings in which like reference numbers refer to like elements, FIG. 1 is a block diagram of the apparatus and system of the present invention. A kinematic data capture device 10 is configured and disposed to capture kinematic data of a subject in motion. As detailed below, data capture is frequently by optical means, but other capture systems are within the scope of the present invention. The kinematic data capture device 10 yields time and position data for any number of points on a subject body. These may be organized for example in a spreadsheet. These data 12 are output by the kinematic data capture device 10 and made available to processor or computer 30.

The kinematic data capture device 10 is also configured to observe, isolate, define and capture body segment dimensional data. This data is also output 14 into a database or other digital format which may be accessed by the computer or processor 30. Segment dimension data may for example include three points located on a body segment. For example, for any rigid body segment such as the upper arm, a first joint, a second joint and a midpoint may be defined, as for example, a shoulder, elbow and bicep, respectively. Distances of these points may be included among the segment dimensional data. The distances may be relative to the other position points for that segment or to another reference point. As detailed below, one method of identifying body segment points is by the attachment to them of a reflector, which may then be observed during a subject's motion by the kinematic data capture device 10. The kinematic data capture device is an operative communication with the processor or computer 30 in a manner such that data collections 12 and 14 may be transferred to or accessible by the computer 30.

Mass data capture device 20 is configured and disposed to obtain mass data on a subject. This data may be subdivided into body segments. These segments may correspond to the segments defined and observed by the kinematic data capture device 10. The mass data capture device 20 is in operative communication with computer 30 such that mass data it obtains is accessible by the computer for use and further calculations. In the depicted embodiment, the mass data capture device is separate from the kinematic data capture device and may be a DXA device, as described more fully below.

Computer or processor 30 is configured to access the segment dimensions data 14 in order to aid in the calculation of lever and force moments. In the depicted embodiment, these calculations may comprise a first step of calculating a centroid for a given body segment.

In the depicted embodiments, both mass data and kinematic data are captured of the entire subject, i.e., the subject's whole body.

The computer 30 is further configured to calculate velocity and acceleration data and, if desired, jerk data from the time and position database 12. The computer 30 is further configured to calculate the centroid 34 as described above. With the centroid and segment dimensions defining a moment, the computer 30 calls up segment mass data from the mass data capture device database and therewith calculates a force data 36 for a user selectable position and direction. In the depicted embodiment, all data is configured in a Cartesian coordinate system. Accordingly, a force in a user selectable plane may be calculated as an output 38.

FIG. 2 is a flowchart of the method of the present invention. First kinematic data is obtained 110. The next mass data is obtained 120. These two steps may be performed in any order. Segment dimensions are obtained using the kinematic data captured at step 122. Time and position data from the kinematic database are used to generate velocity, acceleration, and if desired, jerk data at step 124. Next for a user selectable body segment a centroid is calculated at step 126. Next a moment arm is calculated at step 128 using the body segment dimensions and centroid data. Next a mass data is called up and identified for the selected body segment at step 130. Thereafter, one or more of the following outputs may be calculated: a force 136, or a torque 138 for a designated joint.

Kinematic Data Capture Device

Motion capture, motion tracking, or mocap are terms used to describe the process of recording movement and translating that movement onto a digital model. Initially invented in Scotland, it is used in military, entertainment, sports, and medical applications. In filmmaking it refers to recording actions of human actors, and using that information to animate digital character models in 3D animation.

In motion capture sessions, movements of one or more subjects are sampled many times per second, although with most techniques (recent developments from ILM use images for 2D motion capture and project into 3D) motion capture records only the movements of the subject, not his/her visual appearance. This animation data is mapped to a 3D model so that the model performs the same actions as the actor.

Camera movements can also be motion captured so that a virtual camera in the scene will pan, tilt, or dolly around the stage driven by a camera operator, while the actor is performing and the motion capture system can capture the camera and props as well as the actor's performance. This allows the computer generated characters, images and sets, to have the same perspective as the video images from the camera. A computer processes the data and displays the movements of the actor, providing the desired camera positions in terms of objects in the set. Retroactively obtaining camera movement data from the captured footage is known as match moving.

Optical systems utilize data captured from image sensors to triangulate the 3D position of a subject between one or more cameras calibrated to provide overlapping projections. Data acquisition is traditionally implemented using special markers attached to a subject; however, more recent systems are able to generate accurate data by tracking surface features identified dynamically for each particular subject. Tracking a large number of performers or expanding the capture area is accomplished by the addition of more cameras. These systems produce data with 3 degrees of freedom for each marker, and rotational information must be inferred from the relative orientation of three or more markers; for instance shoulder, elbow and wrist markers providing the angle of the elbow.

Optical: Passive Markers

Passive optical system use markers coated with a retroreflective material to reflect light back that is generated near the cameras lens. The camera's threshold can be adjusted so only the bright reflective markers will be sampled, ignoring skin and fabric.

The centroid of the marker is estimated as a position within the 2 dimensional image that is captured. The grayscale value of each pixel can be used to provide sub-pixel accuracy by finding the centroid of the Gaussian.

An object with markers attached at known positions is used to calibrate the cameras and obtain their positions and the lens distortion of each camera is measured. Providing two calibrated cameras see a marker, a 3 dimensional fix can be obtained. Typically a system will consist of around 6 to 24 cameras. Systems of over three hundred cameras exist to try to reduce marker swap. Extra cameras are required for full coverage around the capture subject and multiple subjects.

Constraint software reduces problems from marker swapping since all markers appear identical. Unlike active marker systems and magnetic systems, passive systems do not require the user to wear wires or electronic equipment rather hundreds of rubber balls with reflective tape, which needs to be replaced periodically. The markers are usually attached directly to the skin (as in biomechanics), or they are velcroed to a performer wearing a full body spandex/lycra suit designed specifically for motion capture. This type of system can capture large numbers of markers at frame rates as high as 2000 fps. The frame rate for a given system is often traded off between resolution and speed so a 4 megapixel system runs at 370 hertz normally but can reduce the resolution to 0.3 megapixels and then run at 2000 hertz.

Optical: Active Marker

Active optical systems triangulate positions by illuminating one LED at a time very quickly or multiple LEDs with software to identify them by their relative positions, somewhat akin to celestial navigation. Rather than reflecting light back that is generated externally, the markers themselves are powered to emit their own light. Since Inverse Square law provides ¼ the power at 2 times the distance, this can increase the distances and volume for capture.

The power to each marker can be provided sequentially in phase with the capture system providing a unique identification of each marker for a given capture frame at a cost to the resultant frame rate. The ability to identify each marker in this manner is useful in realtime applications. The alternative method of identifying markers is to do it algorithmically requiring extra processing of the data.

Optical: Time modulated active marker high-resolution active marker system with 3,600×3,600 resolution at 480 hertz providing real time submillimeter positions.

Active marker systems can further be refined by strobing one marker on at a time, or tracking multiple markers over time and modulating the amplitude or pulse width to provide marker ID. 12 megapixel spatial resolution modulated systems show more subtle movements than 4 megapixel optical systems by having both higher spatial and temporal resolution. The unique marker IDs reduce the turnaround, by eliminating marker swapping and providing much cleaner data than other technologies. LEDs with onboard processing and a radio synchronization allow motion capture outdoors in direct sunlight, while capturing at 480 frames per second due to a high speed electronic shutter. Computer processing of modulated IDs allows less hand cleanup or filtered results for lower operational costs. This higher accuracy and resolution requires more processing than passive technologies, but the additional processing is done at the camera to improve resolution via a subpixel or centroid processing, providing both high resolution and high speed. These motion capture systems are typically an eight camera, 12 megapixel spatial resolution 480 hertz system with one subject.

IR sensors can compute their location when lit by mobile multi-LED emitters, e.g. in a moving car. With Id per marker, these sensor tags can be worn under clothing and tracked at 500 Hz in broad daylight.

Optical: Semi-Passive Imperceptible Marker

One can reverse the traditional approach based on high speed cameras. Systems such as Prakash use inexpensive multi-LED high speed projectors. The specially built multi- LED IR projectors optically encode the space. Instead of retro-reflective or active light emitting diode (LED) markers, the system uses photosensitive marker tags to decode the optical signals. By attaching tags with photo sensors to scene points, the tags can compute not only their own locations of each point, but also their own orientation, incident illumination, and reflectance.

These tracking tags that work in natural lighting conditions and can be imperceptibly embedded in attire or other objects. The system supports an unlimited number of tags in a scene, with each tag uniquely identified to eliminate marker reacquisition issues. Since the system eliminates a high speed camera and the corresponding high-speed image stream, it requires significantly lower data bandwidth. The tags also provide incident illumination data which can be used to match scene lighting when inserting synthetic elements. The technique appears ideal for insitu motion capture or real-time broadcasting of virtual sites but has yet to be proven.

Optical: Markerless

Emerging techniques and research in computer vision are leading to the rapid development of the markerless approach to motion capture. Markerless systems do not require subjects to wear special equipment for tracking. Special computer algorithms are designed to allow the system to analyze multiple streams of optical input and identify human forms, breaking them down into constituent parts for tracking.

Commercial solutions for markerless motion capture may be used, including a real-time system by Organic Motion™.

Non-Optical Systems

Inertial Systems

Inertial Motion Capture technology is based on miniature inertial sensors, biomechanical models and sensor fusion algorithms. It's an easy to use and cost-efficient way for full-body human motion capture. The motion data of the inertial sensors (inertial guidance system) is transmitted wirelessly to a PC or laptop, where the full body motion is recorded or viewed. Most inertial systems use gyroscopes to measure rotational rates. These rotations are translated to a skeleton in the software. Much like optical markers, the more gyros the more natural the data. No external cameras, emitters or markers are needed for relative motions. Inertial mocap systems capture the full six degrees of freedom body motion of a human in real-time. Benefits of using Inertial systems include; No solving, freedom from studios as most systems are portable, and large capture areas. These systems are similar to the Wii controllers but much more sensitive and having much greater resolution and update rate. They can accurately measure the direction to the ground to within a degree. The popularity of inertial systems is rising amongst independent game developers, mainly because of the quick and easy set up resulting in a fast pipeline. A range of suits are now available from various manufacturers.

Mechanical Motion

Mechanical motion capture systems directly track body joint angles and are often referred to as exo-skeleton motion capture systems, due to the way the sensors are attached to the body. A performer attaches the skeletal-like structure to their body and as they move so do the articulated mechanical parts, measuring the performer's relative motion. Mechanical motion capture systems are real-time, relatively low-cost, free-of-occlusion, and wireless (untethered) systems that have unlimited capture volume. Typically, they are rigid structures of jointed, straight metal or plastic rods linked together with potentiometers that articulate at the joints of the body. These suits may have an external absolution positioning system.

Magnetic Systems

Magnetic systems calculate position and orientation by the relative magnetic flux of three orthogonal coils on both the transmitter and each receiver. The relative intensity of the voltage or current of the three coils allows these systems to calculate both range and orientation by meticulously mapping the tracking volume. JZZ Technologies™ uses this hardware in their E-Factor motion capture analysis program. The sensor output is 6DOF, which provides useful results obtained with two-thirds the number of markers required in optical systems; one on upper arm and one on lower arm for elbow position and angle. The markers are not occluded by nonmetallic objects but are susceptible to magnetic and electrical interference from metal objects in the environment, like rebar (steel reinforcing bars in concrete) or wiring, which affect the magnetic field, and electrical sources such as monitors, lights, cables and computers. The sensor response is nonlinear, especially toward edges of the capture area. The wiring from the sensors tends to preclude extreme performance movements. The capture volumes for magnetic systems are dramatically smaller than they are for optical systems. With the magnetic systems, there is a distinction between "AC" and "DC" systems: one uses square pulses, the other uses sine wave pulse.

Mass Data Capture Device

Dual Energy X-ray Absorptiometry (DXA, Previously DEXA)

Use of dual energy X-ray absorptiometry (DXA, previously DEXA) for total body screening is the most accurate means of body composition analysis available today. While this scan has traditionally played a role in the non-invasive measurement of skeletal bone status, this scan is also able to provide specific measures of lean and fat tissue components including fast, lean muscle mass, etc. This is an exceptional clinical method for body composition screening because of its low dose of radiation, speed, ease of application, and accuracy. The amount of radiation that a participant receives from the DXA scan is 0.1 mrem, considerably lower than the typical radiation exposure from a normal chest x-ray which is 20 mrem. It is important to note that information obtained from DXA scans performed are not used in diagnosis. These scans aid in the full examination of the body composition of the athlete. For more details on the use of the DXA information in the present process, please refer to the section entitled 'Significance'.

Subject Testing and Data Collection

When an athlete is evaluated using the present invention, they will proceed through three specific phases of testing and data collection. These phases each take place with three different staff members.

Subjects will be given a detailed written survey inquiring after their physical condition, including particularly injuries. The survey may ask for a graphic identification of an injured body part, such as by an X on a drawing of a figure. The survey may continue to ask past injuries. The survey may be organized according to body parts for example, including neck, shoulder, upper arm, elbow/forearm, wrist/hand/fingers, spine/low back/sacroiliac joint, ribs/thorax/chest, hips/groin, thigh, knee, ankle/lower leg, foot/toes. Each body part portion of the survey may ask after injury histories, description of the injuries, dates of injuries and severity such as the amount of time missed. Diagnostic tests can be inquired after and of course medical care such as surgery for the injury. Ongoing medical care or support such as for example braces needed may be discovered with using this survey.

Phase 1: Meeting with the Exercise Physiologist: The Exercise Physiologist is knowledgeable in the field of physiological evaluations including stress testing, strength testing, or endurance testing. This person can examine how athlete's body is responding to acute exercise as well as chronic exercise training.

Phase 2: Meeting with the Physical Therapist or Athletic Trainer: This person is knowledgeable in the areas of injury prevention and injury care. They evaluate muscle imbalances and rehabilitate athletes from injury.

Phase 3: Meeting with the Biomechanist: This person is knowledgeable in the fields of movement and physics. They identify kinematic variables (speed, velocity, etc.) and kinetic variables (forces) that the athlete experiences during movement.

First the subject, who may be an athlete, will have an office meeting with the exercise physiologist. During this meeting the exercise physiologist will discuss the past and present health of the athlete. The athlete is asked to complete a thorough questionnaire of current and past injuries. The Exercise Physiologist reviews this document and asks the athlete any questions that may arise based on the reviewed answers. The physiologist will also collect information on the past (3 years) training programs the athlete has completed. All of this will be collected and documented for future use.

During this meeting if the exercise physiologist feels specific physiological testing is necessary they may have the athlete perform those tests. If this testing has been performed recently by the athlete's coaching staff this may not be necessary. Additionally, a Dual Energy X-ray Absorptiometry (DXA) scan will be administered for data collection related to body composition. By the end of the meeting the exercise physiologist will have determined whether or not this athlete is able to participate in the next phases of testing.

If further collection will take place at a later date scheduling for the next meeting will then take place. If the athlete has performed any physiological testing during this session, with the exception of the DXA scan, further testing will take place no earlier than one week later.

Before the second phase of athlete testing and collection begins the exercise physiologist, physical therapist, and biomechanist will review the phase one results as these will help to guide the team through the remaining phases.

Next, the athletes will meet with the physical therapist or athletic trainer to go through a complete movement physical. At this time the therapist or trainer will evaluate mobility at each joint and assess posture or any other physical attribute addressed in the past injury history of the athlete or the current visual inspection of the athlete. This information is collected and documented for future use.

Next, the athlete will move to the testing area and be asked to wear either a spandex suit or the specialized motion capture suit provided by DARI. The spandex suit will allow for staff to place markers directly on the skin if the motion capture suit does not fit or is inappropriate for testing. The motion capture suit is designed for ease of marker attachment to the athlete. Once the athlete is in proper attire they will be led through a sport specific warm-up. This warm-up can be altered depending on the athlete's current injury status or suggestions from the athlete's health care staff.

Lastly the athlete will be asked to perform two protocols for biomechanical data collection.

Athlete Movement Diagnostic (Refer to FIGS. 3-7)

Sport and position specific fatiguing protocol (Refer to FIGS. 3-7)

1—Athlete Movement Diagnostic

After the athlete has completed phase 2 they will move into the capture volume areas of the motion capture system. This camera system allows for a 3-dimensional recording of the athlete. At this time the athlete will start in a common base position designated the "T pose" in the center of the capture volume. Following the T pose positioning the athlete is asked to do common movements.

These movements include but are not limited to: Wrist flexion and extension, elbow flexion and extension, shoulder abduction and adduction, shoulder internal and external rotation, shoulder flexion and extension, Trunk rotation, pelvic tilt, squat, vertical jump, lunges, single legged jump for height, single legged jump for distance, and single legged 4 corner speed jumps.

Each recorded file is collected independently and combined to give us one sheet of information followed by graphical outputs of designated areas of importance noted by the user. Please refer to Appendices 4 and 5 for the detailed reports.

2—Sport/Position Specific Fatiguing Protocol

Directly following the Athlete Movement Diagnostic the athlete will begin to perform a protocol that involves movement the athlete will most commonly perform in their sport. For example, a quarterback in football would throw a football, a baseball pitcher would pitch a baseball, and golfer would swing a club. The movements that the athletes utilize in their sports will be what they do in the protocol. No motion is untrackable—running, jumping, throwing, swinging are the generic movements that most will involve but extremely specific models can be designed. Alternatively, a rehabilitation subject may perform activities of daily living that may need improvement.

Protocol designs will be structured as follows: 1) sport/position specific movement, 2) fatiguing exercises, and 3) Repetitions.

During the sport/position specific movement protocol an athlete will repeatedly perform a movement deemed specific to their sport. For example, a football quarterback will throw up to 10 passes in one set of movements before moving on to the fatiguing exercises. The fatiguing exercises are designed to stress and fatigue the same movements, muscle groups, and energy systems involved in the sport or position (i.e. medicine ball throws and agility drills). Following the fatiguing set of exercises the athlete will immediately move back into the sport/position specific movement analysis again (i.e. 10 more passes for the quarterback). The cycles will be timed and structured so that the athlete reaches a high level of fatigue. Cycles can be added or subtracted depending on the level and physical state of the athlete. Refer to FIG. 6 for the calculations associated with this process.

Once the collection process is completed the data gained through the analysis will be broken down into each sport/position specific movement set (i.e. throwing), and an overall totals page for various variables of interest (i.e. specific range of motion of the shoulder) using the software. This will also allow the staff to examine average values for each variable of interest as well as highs and lows found for each variable tracked. For an example of this output refer to FIG. 7.

When the collection process is over the athlete and their staff have completed all of their work needed to be done for the session, equipment will be broken down and stored appropriately. The staff will compile all the results.

After the athlete testing and data collection process the team will combine notes from all analyses performed on the athlete by the Exercise Physiologist, Athletic Trainer/Physical Therapist, and Biomechanist to find common threads in their evaluations. Specific trends of movement mechanics can lead to reasoning for joint or muscle pain. These can also be traced to current or past training programs. The opposite of this is true as well—athletes performing specific movement patterns as the result of muscle imbalances may be predisposing themselves to injury even if they are not yet in pain.

One goal of the process is to address the athlete's mechanics, adjust these mechanics through therapy, and adopt new training programs as needed. All of this information may be found collectively in one file such as a "Performance Profile". This profile includes results and notes on all information collected on the athlete. This includes everything from health history, motion capture data, to comments from each professional. This file may be presented to the athlete or their health care staff with full explanation over the findings.

Motion Capture Equipment Arrangement

The set up of the equipment and system used for the movement analyses needs to have to the functionality to accommodate: 1—The camera system being used, 2—the number of cameras used in the system, 3—the movement being examined inside the capture volume, and 4—the movement being utilizing outside the capture volume.

For the camera system being used, depending on the system, space may or may not be an issue. All optical 3D cameras have to be housed indoors because UV light can effect marker tracking. Therefore, this type of system will need to be strategically set up to utilize space in a gym or wide open indoor space. Other systems like active or non-optical systems do not necessarily have these complications. These can be used in UV light settings and therefore can be taken outside. Space is no longer an issue when using these systems. Lastly, power supply to the system can be a challenge as well and can also limit the amount of usable space. Indoor turf or basketball surfaces may be used for testing.

With regard to the number of cameras, motion capture technology may use at least 3 cameras to triangulate a spot in 3 dimensional space. Most systems use at least 6-8 cameras for full body motion capture, but at least 12 cameras is preferred. The more the cameras the more likely markers will not be dropped or blocked, allowing for a more complete picture of the movement. Additional cameras are added to the system for analysis of a more complicated movement. Most systems can handle 16 to 30 total cameras. Strategy lies in placement of the cameras. One set up for a 12 camera system may be a hexagon shape with tripods and 2 cameras on each tripod. This arrangement allows for maximal overlap of space and insures at least 3 cameras are in sight of each marker.

Next, the capture volume is appropriately defined. If an athlete is throwing a ball or swinging an object the space they will be moving about changes. That space may be evaluated to make sure that the capture volume fits the specific movement appropriately. If athletes are squatting low to the ground (i.e.—a 3 point football stance, or prepping for a shot put throw) cameras need to be placed so that all markers can be seen by at least 3 cameras. The shape of the camera arrangement may vary as well. Different models can be designed and implemented to fit accordingly. The objective is to optimize marker visibility.

Any space needed outside the capture volume must be provided. When an athlete is performing their sport specific movement must ensure the space will accommodate their movement. For example, a throwing athlete needs enough space outside the capture volume to throw the object. A running athlete will need enough space at accelerated or decelerate for their movements. Furthermore, the combination between the motion capture space and space outside the capture zone need to be set up correctly so that they athletes are moving in the correct planes (i.e. athletes don't run into tripod poles during their drills).

Refer to FIG. 8 for a graphic representation of the motion capture equipment arrangement.

In these ways, the invention may track both kinematic and kinetic variables without the use of a force plate. The invention may advantageously measure while fatiguing the athlete appropriately to induce changes that could be detrimental to their performance.

Kinematic variables related to movement (velocity, range of motion, etc.), may be tracked. A force plate can also collect some kinetic data as well. A force plate is a square platform that can give information about ground reaction forces. This is a great piece of equipment but it is very small and you can only fit one step worth of motion during gait onto the force plate. Because of this limited space only one step at a time may be tracked which can be very unhelpful in a two step gait, or during examination of complex movement patterns. Furthermore, because of the small size of the force plate, athletes generally will change their movement patterns in order to land directly on a specific area of the force plate. Thus, the athletes' movements are different than they would be if they were not told where to step. Institutions collecting force data through the use of a force plate are not obtaining all of the information that is necessary to breakdown and understand human movement. All of these issues collectively demonstrate a problem when calculating forces acting on the body through the use of a force plate.

The present invention calculates all of these forces without the use of a force plate. The DXA scan provides us with the specific body mass of the whole individual as well as specific segments of their body. Using this information combined with acceleration data from the FULL body motion capture analysis we are able to apply Newton's 2nd law of physics (A force generated in one direction creates and equal and opposite force in the opposite direction) and sum the force in each direction for the entire body. This data will allow athletes to calculate forces on the body in any location inside the capture volume of the motion capture system. Instead of a small plate and only one step with unnatural movements, the invention process, using inverse dynamics, can calculate any possible movement. As long as the cameras can see the markers these variables can be calculated.

Kinematic variables are helpful in these analyses but become flat and meaningless if they are not combined with kinetic data. Athlete's kinematics can be extremely similar between each movement but the kinetic chain from the ground to the athlete's appendages can be very different between each movement. Being able to measure these forces, which the human eye can not see, gives great insight into high stress zones on the body which can help athletes avoid overuse injuries or even chronic pain. All of these new insights can help change an athlete's movement patterns and ultimately lead to performance improvements.

Fatiguing the athlete appropriately to induce changes that could be detrimental to their performance provides advantageous measurements. Prior performance based biomechanical evaluations never look at the results of an athlete once they are fatigued. As stated earlier, kinematic variables don't change significantly over the course of a training bout. That is what was observed in the prior art. So, naturally if they don't change then why track that variable. However, adding in the kinetic data we can more fully see what really happens to the athletes' mechanics when they fatigue and track possible changes in mechanics that are adopted as a result. New movement patterns lead to injuries. Understanding when the athlete is fatigued and the mechanical response to fatigue will give more knowledge to help athletes avoid injury.

Furthermore, physiological markers such as those found in blood markers can be related to fatigue and inflammation to track whether or not the athlete is truly fatigued. This information can be matched to the biomechanical results which can be transferred directly to game time situations. If physiological markers indicated the athlete is fatigued, that can be correlated with mechanics that are being utilized and judge whether or not the athlete is at a higher risk for injury.

With enough cameras, the invention can collect unbroken chains for the forty yard dash or one hundred meter sprint and give information on every step. This will allow us to understand when top speed occurs and for how long one can maintain top speed. This information can be directly transferred to the training environment.

Hence the invention advantageously provides for the measurement and analysis of full body movements, such as sprinters leaving blocks, jumping, cutting, gymnastic movements and the like, due at least to the elimination of the need for force plates.

The data further provides for the calculation of torques on specific joints and the isolation of metrics such as force by a plane of interest, such as the saggital plane.

An analysis on any athlete, can be stored as a baseline testing session. This information can be used at a later data in the event of an injury. This information can be used as a ruler for comparison used in post injury rehabilitation. The next step in sports medicine is to provide this baseline for comparison. This data can be used as an objective tool to determine when an athlete is back to "100%". This will allow athletes or teams to track performance before injuries, after injuries, and as the athlete ages.

FIGS. 8 and 9 show one layout of a kinematic data capture device. A plurality of tripods 210 each hold 2 cameras 212. The tripod set up for cameras has two cameras adjusted to view high or low regions overlapping in the center of the calibrated space. This will help optimize the calibration of the motion capture system and increase your capture volume to the largest size possible.

The cameras are in operative communication with a computer 230, here through hardwiring 214. The cameras are deployed to define a capture zone 220. The capture zone 220 may have a movement progression area.

In the depicted embodiment, x and z coordinates are on a coronal plane. The Z plane always points away from the computer.

In the depicted embodiment, cameras (illustrated as reference numbers 1-12 in FIG. 8) are set up in a hexagonal shape. Two cameras on are on each tripod, providing collection of a high and a low range. No wires are in the movement progression area. The computer station is behind the direction of movement. The movement progression area needs to accommodate the movement. i.e. if a person is running they need enough space to complete their run. If an athlete is throwing they need enough space to complete the throw. This can be a substantial space.

Some cameras are affected by UV light, so indoor setting are mandatory with some equipment and direct light from windows needs to be avoided.

Calculations

DEXA values are given in grams. These may be converted into kilograms. The percentage distribution of each limb found in Dempsters parameters may be used to determine the segments mass.

Velocity, Acceleration, Jerk are calculated from the extensive time and position data gathered by the kinematic data capture device.

$$\frac{\text{Change in } Distance^2 - \text{Change in } Distance^1}{\text{Change in } Time^2 - \text{Change in } Time^1}$$

$$\frac{\text{Change in } Velocity^2 - \text{Change in } Velocity^1}{}$$

$$\frac{\text{Change in } Acceleration^2 - \text{Change in } Acceleration^1}{\text{Change in } Time^2 - \text{Change in } Time^1}$$

As shown in FIG. 10, the joint angle calculation is an example of an elbow angle where (S) represents the shoulder marker, (E) represents the elbow marker, and (W) represents the wrist marker. Angle A is the angle that is defined. This is applied to every joint, as follows.

$$L(a) = \sqrt{(x_S - x_E)^2 + (y_S - y_E)^2 + (z_S - z_E)^2}$$

$$L(b) = \sqrt{(x_W - x_E)^2 + (y_W - y_E)^2 + (z_W - z_E)^2}$$

$$L(c) = \sqrt{(x_S - x_W)^2 + (y_S - y_W)^2 + (z_S - z_W)^2}$$

$$A = \arccos[b^2 + c^2 - a^2/2(b)(c)]$$

Radians $X(180/\Pi)$=Degrees

Determining the 3D center of gravity or moment is illustrated with reference to FIG. 11. Dempster's data for anthropometrics can be used to calculate each segment the center of gravity as a percentage of length. Once the length from each joint to the center of mass is known, directional components may be derived. For example, if the lower leg is 10 inches long and the center of gravity is found 40% from the proximal end, then distance A is 4 inches. Furthermore, from the motion capture system the distance of (b) and (c) may be derived, which are in the same ratio as the length of (a). Therefore the length to the center of mass in each of its components is obtained. This is extremely important when adding in gravity. This is a dynamics calculation.

The markers placed on the body advantageously have at least 3 markers per segment. Those three markers can help triangulate a rigid body for each segment. That information may then be transposed to the center of gravity. This is not a gross adjustment.

Calculating Force may now be calculated with the data collected and derived above, and advantageously done without reliance on a force plate. The collected information above calculates force with the equation of Force=Mass*Acceleration, where the mass is found in the DEXA information and the acceleration from the center of gravity collected by the motion capture system.

Summation of Forces and Distribution between each foot is illustrated with reference to FIG. 12. Each segment of the body has a force needed to move each segment. The summation of those forces in each of its planes is equivalent to information previously found only with a force plate. The force is distributed from any part of the body in contact with the ground. Most movements involve 1-2-or 3 contact points on the ground. An example of this is two feet on the ground. If both feet are on the ground the summed force may be correctly distributed.

The distribution of the force is determined on the center of gravity of the entire person. As that shifts with relation to its distance to each foot, the weight percentage of the force also shifts. In the example the distance between each foot is 100% of the total distance. From each respective foot to the center of gravity is divided into its percentage from the total distance (Both percentages always equaling 100%). The force distribution for each foot is opposite its percentage distance from the center of gravity. As a result, the right foot is 70% of the distance away from the center of gravity but only holds 30% of the load.

The ground is predetermined as a certain plane. When a foot leaves that plane 0 force is loaded to that limb and 100% is delivered to the other leg if in contact with the ground.

Joint Torque/Moment Calculation may be calculated as well from the force for each segment and distribution of each to give you the forces acting on each joint. This is done as depicted with inverse dynamics and working from the ground up to the joint of Moment(Joint Torque)=(Ankle Force in the $x$ plane (or $z$ plane))*(Distance to the center of the foot in the $y$ plane)+(Ankle Force in the $y$ plane)*(Distance to the center of the foot in the $x$ plane (or $z$ plane))+(Inertia)*(Angular Acceleration).

Inertia=(weight of the foot)*(length of the foot*Radius of Gyration)$^2$

All the information needed for these calculations can be found advantageously with only the DEXA, a few charts, and the position and time data gathered from the motion capture system.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A physical evaluation system comprising:
   a kinematic data capture device, said kinematic data capture device being configured and disposed to obtain whole body kinematic data from a subject;
   said kinematic data capture device being further configured to obtain dimensions of at least one body segment;
   a mass data capture device; said mass data capture device being configured and disposed to obtain mass data on the subject, said mass data being separable according to body segments of a subject to yield segment mass data;
   a processor, said processor being configured to calculate a force using in combination said kinematic data, said body segment dimensions and said segment mass data, said force being generated by a subject of said physical evaluation system at selectable positions or in a selectable direction;
   said force being calculated without a force plate.

2. The system of claim 1 wherein said kinematic data capture device is optical.

3. The system of claim 2 wherein said kinematic data capture device uses optical markers.

4. The system of claim 3 wherein said kinematic data capture device uses active optical markers.

5. The system of claim 1 wherein said kinematic data capture device is inertial.

6. The system of claim 1 wherein said kinematic data capture device is mechanical.

7. The system of claim 1 wherein said kinematic data capture device is magnetic.

8. The system of claim 1 wherein said kinematic data capture device uses cameras.

9. The system of claim 8 wherein said cameras are deployed to move relative to the subject during data capture.

10. The system of claim 1 wherein the subject is human.

11. The system of claim 1 wherein said mass data capture device is a DXA.

12. The system of claim 1 wherein said kinematic data, said segment mass data and said body segment dimensions are captured and results calculated without the use of a force plate.

13. The system of claim 1 wherein said kinematic data capture device is deployed to capture full body movements.

14. A system for conducting a physical evaluation of a subject, said system comprising:
   a kinematic data capture device having a capture volume suitable for said subject to perform a sport specific movement therein, said kinematic data capture device being configured to obtain kinematic data from said subject and to obtain dimensions of at least one body segment;
   a mass data capture device, said mass data capture device being configured to obtain mass data on said subject, said mass data being separable according to body segments of said subject to yield segment mass data; and
   a processor, said processor being configured to calculate a force using in combination said kinematic data, said body segment dimensions and said segment mass data, said force being generated by said subject at selectable positions or in a selectable direction;
   said system being configured for calculating force without the use of a force plate.

15. The system of claim 14 wherein said processor is configured to calculate an acceleration of said body segment using said kinematic data and subsequently combining said calculated acceleration with said segment mass data to calculate force.

16. A method for conducting a physical evaluation of a subject, said method comprising the steps of:
   providing a mass capture data device;
   obtaining mass data on said subject using said mass capture data device, said mass data being separable according to body segments of said subject to yield segment mass data;
   providing a kinematic capture device;
   obtaining whole body kinematic data from said subject using said kinematic capture device;
   obtaining dimensions of at least one body segment using said kinematic capture device;
   calculating a force using in combination said segment mass data, said kinematic data and said body segment dimensions said force being generated b said subject at selectable positions;
   wherein said force is calculated without the use of a force plate.

17. The method of claim 16 further comprising the step of calculating a torque for a joint connecting two body segments.

18. The method of claim 16 further comprising the steps of:
   calculating an acceleration of said body segment using said kinematic data; and
   combining said calculated acceleration with said segment mass data to calculate force.

* * * * *